United States Patent [19]

Finkelstein

[11] 4,119,537

[45] Oct. 10, 1978

[54] METHOD FOR SLIME CONTROL

[76] Inventor: Hershel Finkelstein, 413 Beach 121 St., Rockaway Park, N.Y. 11694

[21] Appl. No.: 792,464

[22] Filed: Apr. 29, 1977

[51] Int. Cl.$^2$ ............................................. C02B 3/06
[52] U.S. Cl. ........................................ 210/64; 71/67; 162/161; 424/159
[58] Field of Search .............. 71/67; 162/161; 210/64; 424/158–160

[56] References Cited

U.S. PATENT DOCUMENTS

| | | | |
|---|---|---|---|
| 1,343,034 | 6/1920 | Cheeseman | 424/159 |
| 2,878,155 | 3/1959 | Cruickshank | 210/64 |
| 3,948,636 | 4/1976 | Marks | 71/67 |
| 4,018,679 | 4/1977 | Bolsing | 210/59 |
| 4,043,911 | 8/1977 | Melnick et al. | 210/64 |

*Primary Examiner*—Thomas G. Wyse
*Attorney, Agent, or Firm*—J. B. Felshin

[57] ABSTRACT

These chemical formulations and agents are to be used as water treatment agents in industrial water systems to control and improve such factors as bacteriological contamination, pollution and cleanliness. Chemical limes, hydrosulfites and dispersants are used together in a formulation, in relatively low concentrations, to primarily inhibit and destroy slime and microorganisms. No toxicants as such are needed. In addition, the chemical lime particles can be coated to give a delayed and safer reaction with water and to give reduced dusting.

11 Claims, No Drawings

METHOD FOR SLIME CONTROL

GENERAL

Many chemical agents are used to inhibit and control slime and microorganisms in industrial water systems. These chemical agents are generally hazardous to handle and substances which cause pollution in the waste water. The present invention has been found to act as a slime control agent, or biocide, and yet does not contain what is generally known as a toxic agent. The invention is dissolved in industrial water systems at concentrations as low as 5. PPM. By means of the invention, toxic or corrosive biocides such as sulfones, chlorines and phenols are not needed. Testing showed that bacteriological contamination is prevented and reduced considerably by using formulations of the invention and that there are potent and synergistic actions.

One of the most widely used tests for slimicides in the pulp and paper field is called: "Mill Stock Testing of Biostatic Agents," Pulp and Paper 23, No. 1:80, 82–83 (1949). One of the formulations possible by means of the invention showed the following result using this test:

| Concentration | % Kill |
| --- | --- |
| 10 PPM | 26 |
| 25 PPM | 28 |

Formulations of the invention can contain a combination of: a water soluble organic surfactant; hydrosulfite or perborate salt; a pitch dispersant-complexer; antifoaming agent; a chemical lime product. Used in relatively low concentrations. The invention provides for chemical lime products and particles to be coated with a surfactant compound. This coating results in a delayed reaction when added to water. The surfactant compound is preferably a thick, viscous liquid and does not show any reaction with the lime. For example, chemical lime particles were soaked in a 100% active non-ionic surfactant and allowed to dry and harden under low heat. Plurafac RA-20 is made by BASF Wyandotte Corporation, Michigan, and is a primary aliphatic specially oxyalkylated alcohol and is a biodegradable surfactant. Chemical lime particles coated by means of the invention show much less sputtering, violent reaction and quick generation of heat as compared to the uncoated when added to water.

| Example of Coating Formulation | |
| --- | --- |
| Plurafac RA-20 | 10. grams |
| Hi-calcium quicklime | 50. grams |

SLIME CONTROL FORMULATIONS AND METHODS OF USE

A formulation of the invention which was found to be effective at a concentration as low as 5. PPM contained the following:

| Example | |
| --- | --- |
| Hi-calcium and Dolomitic lime | 60. parts |
| Triton X-155: Rohm and Haas Corporation, non-ionic surfactant, alkylarylpolyether alcohol | 5. parts |
| Antifoam, Nopco Corporation, Foamaster | 10. parts |
| Sodium hydrosulfite | 20. parts |
| Pitch dispersants: Tamol and Fleetquest, polymeric dispersants with chelant | 5. parts |

-continued

| Example | |
| --- | --- |
| blended and mixed | |

| Example of General Composition: | |
| --- | --- |
| Chemical lime, coated or uncoated | 10–75parts |
| Sodium or zinc hydrosulfite or perborate | 10–50parts |
| Pitch control agents | 5–35parts |
| Antifoamer | 5–15parts |
| Surfactant | 2–15parts |
| Anhydrous builder salts | 0–25parts |
| blended and mixed | |

For use in pulp and paper best results with surfactant which was found to be non-substantive to pulp fibers. By non-substantive is meant that the surfactant is not absorbed onto the fibers but remains in the water system. An example is Berocell-25, MoDoKemi AB, Sweden: alkylaryl polyetherglycol. By pitch control agent is meant an agent which acts upon natural pitch, however, these agents can often also act upon fillers, dyes, pigments: organic and inorganic. They can function as dispersers, emulsifiers or absorbers and are an integral part of the formulations of the invention. Pitch control agents which are specifically used in formulations of the invention are those described as anionic, polymeric dispersants with chelant.

The inventive formulation may be fed into a water system as a powder, or liquid suspension in water or solvent. Can be added continuously or at intervals. It is of course possible to use the inventive formulation alone, or in conjunction with conventional biocides. Additions can be made at one or more points in the water system to be treated.

TOXICITY

The invention provides for potent biocidal actions, yet does not cause pollution problems in the waste water. The inventive formulations show good percent kill of organisms causing slime and also considerable cleaning power. Cleaning power is shown by making paper handsheets with and without the inventive formulation. Paper handsheets simulate papermaking on a small scale and are widely used in papermaking for testing and evaluation. A sulfone slimicide showed 46% kill slimicide evaluation at 25 PPM. The inventive formulations can be used in papermaking by adding 0.5–3. kilograms at the beater or chests per ton dry papermaking pulp.

| Examples of handsheets of pulp slurries exposed one week: | |
| --- | --- |
| A. no formulation added | many specks |
| B. inventive formulation added at 25.PPM | good appearance |

It can be seen that the inventive formulations give synergistic biocidal and cleaning actions, yet do not contain substances which present problems in the waste water. The pulp slurries were exposed 1 week to air in a metal container. The inventive formulations can be used at a concentration of 5. parts per million, low pH of 6. and short retention time of ½ hour, and, surprisingly exhibit relatively high biocidal properties in aqueous systems.

Table 2

| Concentration | pH | Retention Time | % Kill |
|---|---|---|---|
| 5. PPM | 6.0 | ½ hour | 22. |

Papermaking is often carried out in aqueous systems with a pH of 6. to 6.5.

Chemical limes include dolomitic quicklime, high calcium quicklime and hydrated quicklime. The limes can be coated according to the inventive method. The inventive formulations are toxic to microorganisms which cause slime, yet does not impart color or odor to water or finished product and has no apparent toxicity to fish and birds. It is believed that the inventive formulations contain substances at levels which pose no waste water problems. The inventive formulation may be fed into a water system as liquid suspension in water or solvents.

COATED CHEMICAL LIMES

If 20 grams of hi-calcium quicklime is added to 150.grams of cold water there is an immediate generation of heat and boiling. If chemical lime is first coated as by means of the inventive method, then there is very little generation of heat for 3 minutes. Then a much slower and gradual generation of heat.

| Example: | Hi-calcium lime | Coated Hi-calcium lime |
|---|---|---|
| Reaction with water | immediate | after 3 minutes |
| pH after 30 seconds | 13. | 8. |
| Ph after 3 minutes | 13. | 13. |
| Results: | | |
| Coated lime reacts slower with water compared to uncoated. | | |

Combinations of surfactants can be used to coat the chemical lime particles. The coating can be applied by soaking, mixing or spraying.

It was found that silicates can be included in the coating, and assist to form a stable hard surface. It was found that silicates at weight ratio of $SiO_2/Na_2O$ of 3.75 consistency of thick syrup (Philadelphia Quartz Company) do not react with the lime particles when used 1:1 with the surfactant.

| Example of Coating mixture | | |
|---|---|---|
| $SiO_2/Na_2O$ | 1 part | (PQ S35) |
| Plurafac RA-20 | 1 part | |
| | mixed | |

Chemical limes coated by means of the inventive process can be used also in cleaning formulations, as well as in all kinds of water treatment compositions.

| Example of Laundry Cleaning and Soaking Composition Containing Coated Chemical Lime | |
|---|---|
| surfactants | 40 – 60 % |
| builders | 5 – 25% |
| bleach | 10 – 25% |
| additives and enzymes | 10 – 20% |
| dispersants and foam inhibitors | 0 – 20% |
| coated chemical limes | 0.5 – 20.% |
| mixed and blended solid powder | |

It should be noted that coated chemical limes exhibit reduced dusting in mixing and using. Chemical lime dust caused by handling or mixing limes can be an irritant. The inventive method of coating limes can greatly reduce dusting problems. Coated chemical limes offer improvements in safety and handling during mixing and using. There is a gradual increase in pH with the use of coated lime. Lime is commercially available from the Pfizer Mineral Company, N.Y.,N.Y. and the SI Lime Company, Birmingham, Alabama and lime products include: Quicklime, Rotary Quicklime, Hydrated Lime, Granular Quicklime, Dolomitic Granular Quicklime, and Hi-calcium Quicklime. The particle sizes vary from that which passes a Number 100 sieve to lump lime with a maximum size of 8 inches in diameter.

The invention can be added early in the fiber pulpmaking process, before the bleaching stage, to improve cleanliness and brightness.

EXAMPLE

The invention was evaluated in the wash-water system of a motion picture film processing company. Biocides were necessary to prevent slime buildup and contamination problems.

The invention was used for two weeks, adding every four hours at intervals, in an amount to obtain a concentration of approximately 50 PPM.

The results showed: A clean system and clean film, no slime problems, and no damage to the sensitive color photographic films.

The invention is applicable to treat aqueous systems used for drinking or swimming by humans against slime and to improve sanitation. Treatment is recommended at low concentrations in the range of 0.01 to 2. PPM. The formulation would contain mainly hydrosulfite, lime, and dispersant. The invention is effective against organisms, slime, and contamination. Sodium hydrosulfite and chemical lime products are found on the list of Food Additives, published by the Food and Drug Administration, U.S. Department of Health, Education and Welfare, Section 121.101. Optionally, these formulations can comprise hydrosulfite, lime, and dispersing agent.

| EXAMPLE OF FORMULATION TO PURIFY DRINKING OR SWIMMING POOL WATER | |
|---|---|
| SYSTEM: | |
| Chemical limes | 50 to 90% |
| Sodium hydrosulfite | 10 to 50% |
| Dispersant | 0.5 to 5.% |
| Surfactant | 0.0% to 5.% |
| Antifoaming agents | 0.0% to 5.% |

Dispersants such as propylene glycol, sodium tripolyphosphate, talc, sodium oleate, polyoxyethylene lauryl ether, condensed naphthalene sulfonic acids, and polymeric carboxylic acids, may comprise a part of the invention to assist in the dispersion of the invention and to assist in dispersing contaminating matter found in the aqueous systems treated with the invention.

Liquid dispersions of the invention may be prepared to treat aqueous systems.

I claim:

1. A method for slime control in water systems wherein is added to said water system a chemical formulation comprising chemical lime, pitch dispersing agent, sodium hydrosulfite, antifoaming agent, and a water soluble organic surfactant, wherein the formulation is added to said water system in an amount from 1. to 5,000. parts per million by weight of said chemical formulation, wherein the formulation contains 20 to 80 percent chemical lime, 0.1 to 15. percent water soluble organic surfactant, 5. to 35. percent pitch dispersing agent, 5. to 40. percent sodium hydrosulfite, 1. to 15. percent antifoaming agent.

2. A method according to claim 1 wherein the pitch dispersing agent is an anionic polymeric dispersant with chelant and the water soluble organic surfactant is an non-ionic alkylarylpolyether alcohol.

3. A process according to claim 2 wherein the system is the aqueous system of a pulp fiber and paper mill system.

4. A method according to claim 1 wherein the chemical lime particles are coated with a surfactant, or optionally, with a surfactant-sodium silicate combination.

5. A method according to claim 4 wherein the chemical lime particles are coated with a 100% active non-ionic surfactant in which said surfactant is a primary aliphatic oxyalkylated alcohol.

6. A method according to claim 4 wherein the sodium silicate consists of silica at weight ratio 3.75 to sodium oxide and viscosity of the sodium silicate is 200 to 7,000 centipoises at about 20° centigrade.

7. A process according to claim 1, wherein the aqueous solution includes biocidal formulations.

8. A process according to claim 1, wherein the water system is a laundry cleaning and soaking water solution.

9. A process according to claim 1 wherein the aqueous system is treated with the formulation at a concentration of 3 to 15 parts per million, for a period of ½ to 1 hour, and at a pH of 5 to 8.

10. A process for slime control in aqueous systems wherein is added to said aqueous system a chemical formulation consisting of 60 percent calcium and dolomitic limes, 5 percent anionic polymeric dispersant with chelant, 5 percent nonionic alkylarylpolyether alcohol, 10 percent antifoaming agent, 20 percent hydrosulfite, and wherein the formulation is added to the mill system in an amount from 5 to 100 parts by weight of said formulation, and optionally, the formulation can contain calcium and dolomitic limes coated with the surfactant.

11. A method for slime control in water systems wherein is added to said water system a chemical formulation comprising chemical lime, pitch dispersing agent, sodium hydrosulfite, antifoaming agent, and a water soluble organic surfactant, wherein the formulation is added to said water system in an amount from 0.01 to 5,000. parts per million by weight of said chemical formulation, wherein the formulation contains 20 to 80 percent chemical lime, 0.1 to 15. percent water soluble organic surfactant, 5. to 35. percent pitch dispersing agent, 5. to 40. percent sodium hydrosulfite, 1. to 15. percent antifoaming agent.

* * * * *